United States Patent [19]

Grosso

[11] 4,072,707

[45] Feb. 7, 1978

[54] PREPARATION OF 3,5-DIALKYL-4-HYDROXYBENZOIC ACID

[75] Inventor: Vincent Gerard Grosso, Piscataway, N.J.

[73] Assignee: American Cyanamid Company, Stamford, Conn.

[21] Appl. No.: 738,215

[22] Filed: Nov. 3, 1976

[51] Int. Cl.² .............................................. C07C 65/02
[52] U.S. Cl. ........................... 260/521 C; 260/520 A
[58] Field of Search ............. 260/521 C, 520 A, 473 S

[56] References Cited

U.S. PATENT DOCUMENTS

| | | | |
|---|---|---|---|
| 2,749,362 | 6/1956 | Berni | 260/521 C |
| 3,187,037 | 6/1965 | Giesen et al. | 260/521 C |
| 3,435,068 | 3/1969 | Gehring et al. | 260/521 C |
| 3,532,745 | 10/1970 | Hirao | 260/521 C |
| 3,825,593 | 7/1974 | Meek | 260/521 C |
| 3,870,744 | 3/1975 | Wagner | 260/521 C |

FOREIGN PATENT DOCUMENTS 1,295,429  11/1972  United Kingdom ............. 260/521 C Primary Examiner—Paul J. Killos
Attorney, Agent, or Firm—Philip Mintz

[57] ABSTRACT

A process for preparing a sterically hindered 3,5-dialkyl-4-hydroxybenzoic acid which comprises reacting a sterically hindered 2,6-dialkylphenol with an excess of sodium hydride or lithium hydride in a dry dipolar aprotic solvent, carboxylating the resulting anhydrous phenolate with an excess of carbon dioxide at atmospheric pressure and at a temperature of about 70° C. to 80° C., then destroying the excess sodium hydride or lithium hydride by addition of an alcohol, followed by acidifying the reaction mixture to obtain a high yield of the sterically hindered 3,5-dialkyl-4-hydroxybenzoic acid.

6 Claims, No Drawings

PREPARATION OF 3,5-DIALKYL-4-HYDROXYBENZOIC ACID

This invention relates to a new and improved process for preparing certain old compounds of known utility. More particularly, this invention relates to a new and improved process for preparing 3,5-dialkyl-4-hydroxybenzoic acids from the corresponding 2,6-dialkylphenols.

It is known that 3,5-dialkyl-4-hydroxybenzoic acids wherein at least one of the alkyl groups is branched on the alpha carbon atom are useful per se or as their esters or other derivatives to stabilize polymers against degradation by ultraviolet radiation (see, for instance, U.S. Pat. Nos. 3,112,338; 3,168,492; 3,206,431; and 3,870,680). Generally, for effective stabilization of polymers, it is preferred that each such alkyl group contain 3 to 8 carbon atoms, at least one being branched on the alpha carbon, such as isopropyl, t-butyl, t-octyl, cyclohexyl, sec.-butyl, isopentyl, and the like. Expecially preferred commercially are those derivatives wherein both alkyl groups are t-butyl, that is, derivatives of 3,5-di-t-butyl-4-hydroxybenzoic acid. Other similarly useful examples of such compounds include 3-methyl-5-t-butyl-4-hydroxybenzoic acid, 3,5-diisopropyl-4-hydroxybenzoic acid, 3,5-di-t-octyl-4-hydroxybenzoic acid, 3,5-di-sec-butyl-4-hydroxybenzoic acid, 3-ethyl-5-cyclohexyl-4-hydroxybenzoic acid, 3,5-dicyclohexyl-4-hydroxybenzoic acid, 3,5-di-t-amyl-4-hydroxybenzoic acid, 3-n-propyl-5-sec-butyl-4-hydroxybenzoic acid, and the like. The present invention relates to a new and improved process for preparing this class of compounds.

The Kolbe-Schmitt reaction (see Migrdichian, "Organic Synthesis" Vol. 2 p. 1383-4, published 1957 by Reinhold Publishing Corp., New York or Coffey "Rodd's Chemistry of Carbon Compounds" Vol. III part A p. 306, published 1971 by Elsevier Publishing Co., New York) is a well known process for the manufacture of hydroxybenzoic acids by a heterogeneous gas-solid reaction whereby dry sodium or potassium phenolate is reacted with carbon dioxide under pressure at elevated temperature. This type of heterogeneous gas-solid reaction process and some of the difficulties therewith are briefly outlined in Meek, British Patent 1,219,205, on page 1 lines 41-63.

In attempting to overcome these difficulties of the heterogeneous gas-solid reaction, several processes have been developed for carrying out this reaction in a homogeneous phase, especially for use in converting sterically hindered 2,6-dialkylphenols to the corresponding 3,5-dialkyl-4-hydroxybenzoic acids. Several of these homogeneous phase processes are described in Meek, British Patent 1,219,205; Meek, U.S. Pat. No. 3,825,593; and Ciba-Geigy, British Patent 1,361,558. However, these processes still present operational difficulties.

When a sterically hindered 2,6-dialkylphenol is carboxylated using any of these patented processes, it is necessary to remove either water or a lower alkyl alcohol and at least some of the organic solvent. This requires elevated temperatures (e.g., above about 100° C.) and/or vacuum. At such elevated temperatures, some decomposition of the organic solvent is observed, especially when N,N-dimethylformamide is used. In the Meek process, carboxylation in the presence of the alkali metal alkoxide forms insoluble alkali metal ethyl carbonate, which makes the reaction mixture difficult to stir. Moreover, the process requires careful control of the carbon dioxide added to avoid carbonation of all the alkali metal alkoxide if optimum yields are to be obtained. This is best accomplished by using solid carbon dioxide, but it is difficult to avoid moisture (since "dry ice" readily absorbs moisture) in this method and it is known that moisture will significantly lower yields of the desired 3,5-dialkyl-4-hydroxybenzoic acid.

In accordance with the present invention, a new process has been discovered for the preparation of sterically hindered 3,5-dialkyl-4-hydroxybenzoic acids from the corresponding 2,6-dialkylphenols which process (1) avoids the use of alkali metal alkoxides or alkali metal hydroxides, (2) does not require careful control of carbon dioxide concentration, and (3) avoids the use of elevated temperatures and avoids the necessity for distilling off water or alcohol.

In essence, this new process comprises reacting the sterically hindered 2,6-dialkylphenol with an excess of sodium hydride or lithium hydride in a dry dipolar aprotic solvent, carboxylating the resulting anhydrous phenolate with an excess of carbon dioxide at atmospheric pressure and at a temperature of about 70° C. to 80° C., then destroying the excess sodium hydride or lithium hydride by addition of an alcohol, followed by acidifying the reaction mixture to obtain a high yield of the sterically hindered 3,5-dialkyl-4-hydroxybenzoic acid.

More particularly, in the practice of the process of the present invention, first a slurry is formed by admixing a solution of a 2,6-dialkylphenol in a dry dipolar aprotic solvent with a suspension of sodium hydride or lithium hydride in the same dry solvent. While the solvent used can be any dry dipolar aprotic liquid capable of dissolving the 2,6-dialkylphenol and the lithium phenolate or sodium phenolate formed therefrom (see British Patent 1,361,558 page 2 lines 24–32 and Parker, Chemical Reviews, Vol. 69 (1969) page 2 for definitions and listings of some dipolar aprotic solvents which may be used provided the aforementioned phenols and phenolates are soluble therein), preferred are the N,N-dimethylamides having from 3 to 8 carbon atoms, such as N,N-dimethylformamide, N,N-dimethylacetamide, and N,N-dimethylpropionamide. The sodium hydride or lithium hydride is used in an amount at least equal to that required to form phenolate. Ordinarily, about 1.0 to 5 moles, preferably about 1.25 to 2 moles, of sodium hydride or lithium hydride is used per mole of the 2,6-dialkylphenol. When the phenol and the hydride are mixed at about room temperature, the reaction to form the phenolate causes the temperature of the reaction mixture to rise.

Then, while maintaining the temperature of the reaction mixture at about 70°–80° C., carbon dioxide gas is passed into the stirred reaction mixture below the surface for about 2 to 3 hours. An excess of carbon dioxide, ordinarily up to about a three-fold excess, is added to accomplish the carbonation, although the amount of such excess is not critical.

Thereafter, the reaction mixture is cooled to about room temperature, about 20°-25° C., and a lower alcohol, such as methanol or ethanol, is added to react with and destroy the excess sodium hydride or lithium hydride.

Next, water and a water-immiscible organic solvent, such as benzene, toluene, xylene, trichlorobenzene, etc. are added to the reaction mixture to form a two-phase system wherein the water-soluble sodium or lithium salt of the desired product, 3,5-dialkyl-4-hydroxybenzoic acid, is in the aqueous phase and the water-insoluble materials, such as uncarboxylated phenol and by-products are dissolved in the organic phase.

After separating the phases, the aqueous phase is acidified to a pH of about 2 to 3, which may be by addition of hydrochloric acid or sulfuric acid, causing the 3,5-dialkyl-4-hydroxybenzoic acid to precipitate. After filtration, the product is washed with water and dried. Typically, yields of 90–95% are obtained by this process.

As mentioned previously, especially preferred commercially is the 3,5-dialkyl-4-hydroxybenzoic acid wherein both alkyl groups are t-butyl groups. Accordingly, this invention is further illustrated by the following example showing the preparation of 3,5-di-t-butyl-4-hydroxybenzoic acid from the corresponding 2,6-di-t-butylphenol.

Example

To a reaction vessel is charged 75 ml. of dry N,N-dimethylformamide and 57.6 grams, 1.2 moles, of a 50% dispersion of sodium hydride in mineral oil. The vessel is then purged several times with nitrogen and a solution of 125 grams, 0.606 mole, of 2,6-di-t-butylphenol in 100 ml. of dry N,N-dimethylformamide added thereto slowly. The temperature rises to 70°–80° C. When all of the solution has been added, carbon dioxide gas is introduced below the surface of the stirred reaction mixture at 70°–80° C. for about 3 hours (a three-fold excess is added). The reaction mixture is then cooled to 20°–25° C. and 50 ml. of methanol is slowly added to destroy the excess sodium hydride. Water, 200 ml., is then added along with 50 ml. of toluene. The resulting two-phase system is stirred for 15 minutes and the lower aqueous phase separated. Acidification of the aqueous solution to pH 2–3 with hydrochloric acid causes precipitation of the desired product. The precipitate is filtered, washed twice with water and then dried. 3,5-Di-t-butyl-4-hydroxybenzoic acid, m.p. 208°–212° C. is obtained in about 94% yield.

Similar results are obtained when lithium hydride is used in place of sodium hydride.

I claim:

1. A process for the preparation of sterically hindered 3,5-dialkyl-4-hydroxybenzoic acid wherein at least one of the alkyl groups therein is branched on the alpha carbon atom which comprises reacting a solution in a dry dipolar aprotic solvent of a sterically hindered 2,6-dialkylphenol wherein at least one of the alkyl groups is branched on the alpha carbon with sodium hydride or lithium hydride, the mole ratio of said hydride to said phenol being between about 1.0 and 5; reacting the thus formed phenolate in solution in said dry dipolar aprotic solvent with an excess of carbon dioxide at a temperature of about 70°–80° C.; adding to the resulting reaction mixture sufficient of a lower alcohol to destroy any excess sodium hydride or lithium hydride present therein; forming a two-phase system by adding to the resulting reaction mixture water and a water-immiscible organic solvent; separating the aqueous phase and acidifying to precipitate the 3,5-dialkyl-4-hydroxybenzoic acid.

2. A process as defined in claim 1 wherein said dipolar aprotic solvent is an N,N-dimethylamide having from 3 to 8 carbon atoms.

3. A process as defined in claim 1 wherein the mole ratio of said hydride to said phenol is between 1.25 and 2.

4. A process as defined in claim 1 wherein said alcohol is methanol or ethanol.

5. A process as defined in claim 1 wherein said water-immiscible organic solvent is benzene, toluene, xylene, or trichlorobenzene.

6. A process as defined in claim 1 wherein said phenol is 2,6-di-t-butylphenol.

* * * * *